(12) United States Patent
Gomez Nuñez

(10) Patent No.: US 12,064,095 B2
(45) Date of Patent: Aug. 20, 2024

(54) SYSTEM AND DEVICE FOR THE PREVENTION OF INFECTIONS AND MEASUREMENT OF BODY FLUIDS

(71) Applicant: William Alexis Gomez Nuñez, Ibague (CO)

(72) Inventor: William Alexis Gomez Nuñez, Ibague (CO)

( * ) Notice: Subject to any disclaimer, the term of this patent is extended or adjusted under 35 U.S.C. 154(b) by 676 days.

(21) Appl. No.: 17/277,250

(22) PCT Filed: Aug. 10, 2019

(86) PCT No.: PCT/IB2019/056817
§ 371 (c)(1),
(2) Date: Mar. 17, 2021

(87) PCT Pub. No.: WO2020/058784
PCT Pub. Date: Mar. 26, 2020

(65) Prior Publication Data
US 2021/0315549 A1 Oct. 14, 2021

(30) Foreign Application Priority Data
Sep. 18, 2018 (CO) .................. NC2018/0009806

(51) Int. Cl.
*A61B 10/00* (2006.01)
*A61B 5/20* (2006.01)
*A61F 5/44* (2006.01)

(52) U.S. Cl.
CPC ........ *A61B 10/0045* (2013.01); *A61F 5/4408* (2013.01); *A61B 5/208* (2013.01); *A61B 2010/0077* (2013.01)

(58) Field of Classification Search
CPC .......... A61B 5/20–208; A61B 10/0045; A61B 10/007; A61B 10/0077; A61B 5/14507;
(Continued)

(56) References Cited

U.S. PATENT DOCUMENTS 3,367,332 A 2/1968 Groves
4,658,834 A 4/1987 Blankenship et al.
(Continued)

FOREIGN PATENT DOCUMENTS

EP 0 825 96 A1 6/1983

OTHER PUBLICATIONS

International Search Report on International Patent Application No. PCT/IB2019/056817 dated Mar. 19, 2020 (17 pages).

*Primary Examiner* — David J. McCrosky
(74) *Attorney, Agent, or Firm* — Olson & Cepuritis, Ltd.

(57) ABSTRACT

The present disclosure relates to a device for the measurement of fluids and the prevention of infections caused by probes comprising a module of fluid measurement and a probe infection prevention module. The fluid measurement module comprises an electronic module for the measurement of the body fluids; a disposable container for temporary retention of fluid during measurement; a fluid circulation tube arranged between the probe and the disposable container; and a disposable bag for the final disposal of waste fluids. The probe infection prevention module comprises a sheet equipped with adhesive allowing conformation of a flexible structure to the skin or mucosa of the patient. This module incorporates a gel externally that prevents infections, as well as internal antimicrobial components to inhibit passage of microorganisms through the system. The present invention allows non-invasive measurement of fluids utilizing existing probes while contributing to the reduction of infections in patients.

17 Claims, 13 Drawing Sheets

(58) Field of Classification Search
CPC .. A61F 5/44; A61F 5/453; A61F 5/455; A61F 5/4553; A61F 5/4556; A61M 1/64; A61M 1/65; A61M 2210/1085; A61M 2210/1078; A61M 2210/1089; A61M 2210/1092; A61M 2210/1096; A61M 2210/1082; A61M 27/00; A61M 1/69; A61M 1/70; A61M 1/73; A61M 1/732; A61M 1/734; A61M 1/60; A61G 7/0503; A61J 1/1462

See application file for complete search history.

(56) References Cited

U.S. PATENT DOCUMENTS

| | | | |
|---|---|---|---|
| 5,891,051 | A | 4/1999 | Han et al. |
| 5,902,283 | A | 5/1999 | Darouiche et al. |
| 2009/0062755 | A1 | 3/2009 | Burgess et al. |
| 2009/0314101 | A1 | 12/2009 | Levine |
| 2010/0286559 | A1 | 11/2010 | Paz et al. |
| 2012/0078137 | A1 | 3/2012 | Mendels et al. |
| 2018/0050174 | A1 | 2/2018 | Olson et al. |

SYSTEM AND DEVICE FOR THE PREVENTION OF INFECTIONS AND MEASUREMENT OF BODY FLUIDS

RELATED APPLICATIONS

This application claims the benefit of and priority under 35 U.S.C. 371 to PCT Application No. PCT/IB2019/056817, entitled SYSTEM AND DEVICE FOR PREVENTING INFECTIONS AND MEASURING BODY FLUIDS, filed Aug. 10, 2019; which claims priority to Colombian patent application CO2018009806A, entitled SISTEMA Y DISPOSITIVO PARA LA PREVENCIÓN DE INFECCIONES Y MEDICIÓN DE FLUIDOS CORPORALES, filed Sep. 18, 2018, the entirety of each of which is incorporated by reference herein.

FIELD OF THE DISCLOSURE

The present disclosure is directed to the field of biomedical technology. Specifically, it refers to a fluid measurement and infection prevention device made up of at least two modules: a module for the non-invasive measurement of fluids leaving the human body (e.g., urine, pleural fluid, cerebrospinal, peritoneal, or any other body fluid secretion) and a module that prevents infections triggered by the probes after the loss of natural barriers.

BACKGROUND OF THE DISCLOSURE

Body fluid measurement devices are widely used in the hospital environment, predominantly in the Intensive Care Unit (ICU), but also in hospitalization and emergencies, since they provide valuable data for making therapeutic decisions by treating doctors. The vast majority of fluid measurement devices have a transparent container with an analogous measurement scale, some with mechanical valves, which are coupled with a collection bag for drainage, without processing and transmitting data, or influencing in the prevention of infections triggered by the probes.

Patent application WO2007/079942 discloses a urine measuring device to facilitate and control the measurement of urine in a hospitalized patient. This device comprises a rotating body, with two cavities, housed in an enveloping casing; retention means to prevent movement of the rotating body while collecting urine; detection means that allow the level of urine collected to be measured; and control means indicating when the urine has reached a predetermined level. However, this device is exclusively for urine measurement. Likewise, this device, in addition to being complex, does not contemplate measures to prevent infections, nor means for the processing and sending of data to a user.

U.S. Pat. No. 5,911,786 consists of an apparatus for collecting and measuring a fluid body comprising a measuring container provided with a fluid inlet, a fluid outlet, a valve, and a flexible connection that does not allow the passage of air or fluids and allows axial movement of the valve means with respect to the axis of the measurement container. This device achieves effective sealing of the measuring container. However, the fluid measurement is not accurate, nor is it possible to obtain a record of all measurements. Similarly, it does not deal with the prevention of infections caused by probes.

Patents CN206930346 and CN107063414 disclose a urine monitoring system based on measurement by infrared sensors, in which the data of the weight of the fluid is obtained by weighing; so that, by applying a mathematical formula, the volume of urine can be determined from the weight and density of said fluid. These devices are limited to the measurement of urine. Likewise, they only deal with the weight of the fluid, without foreseeing eventualities such as the reflux of urine or the decrease or prevention of infections due to probes and temporary storage of fluids during measurement.

To prevent infection by probes, other devices have been used. For example, patent application US2014/0370067 discloses a device and a method for disinfection of an insertion channel to prevent catheter sepsis where the disinfection process comprises the application of a viscous or foam-like composition by means of an applicator. The applicator comprises a retention zone that allows the composition to be accommodated. This device only deals with disinfection of probes at the insertion site, but not from the measurement of the fluids that come out of said probe or catheter.

Similarly, U.S. Pat. No. 9,629,983 refers to a catheter dressing whose object is to reduce infections associated with the use of the catheter. The dressing comprises a base connected to a pad and a dressing film, the base, the pad, and the dressing film each have a proximal surface facing the skin of a patient and a distal surface facing away from the skin; where the pad has an antimicrobial agent and the dressing film comprises an adhesive. This dressing only prevents catheter-associated infections, not any type of tube, and does not allow fluid measurement.

BRIEF DESCRIPTION

The present disclosure is directed to a device for measuring body fluids such as urine, blood, cerebrospinal fluid, pleural fluid, peritoneal fluid, or the like, without the need to incorporate additional probes or catheters to those that the patient has, and further accomplishing the foregoing in a precise and safe way by preventing the risk of infections associated with the use of the probe and the fluid measurement device.

The present disclosure refers to a device for the prevention of infections and the measurement of body fluids comprising two modules: a module of non-invasive measurement of body fluids (urine, pleural fluid, cerebrospinal fluid, peritoneal fluid and any other body fluid secretion) and a module for the prevention of infections caused by probes (probes, catheters, tubes, etc.) that channel body fluids after the loss of natural barriers. In some embodiments, the non-invasive fluid measurement module comprises an electronic module (10) that measures the volume in a determined period of time of the evaluated fluid; a fluid circulation tube (27) through which the fluids pass, preventing their reflux and reducing the microbial load that the fluid may contain; a disposable container (8) that temporarily holds fluids while they are being measured; and a bag (24) for the safe disposal of the collected fluids.

In some embodiments, the infection prevention module comprises a sheet of elastic material with a conical shape, which may have adhesive portions that allow the formation of the conical structure, adhesive portions that bind to the probe and adhesive portions that adhere to the skin and/or mucosa of the patient wherein such module is equipped with an antimicrobial gel that prevents the generation of infections at the point of entry of the probe to the patient.

In some embodiments, the antimicrobial gel is also located in the form of a crossbar in the fluid circulation tube (27), in order to achieve control of the microorganisms that pass through the internal part of the system; being located in the middle of these bars the anti-reflux valves that limit the ascent of the fluids. Likewise, in some embodiments, the fluid circulation tube (27) has an expandable cap (33) that avoids direct contact of the external environment with the probes. In some embodiments, the electromechanical valves (21) (22) and the expandable connector (35) for probes also fulfill the anti-reflux function, thereby limiting the rise of microorganisms.

The device according to the systems and methods discussed herein allows the measurement of fluids in a non-invasive way, taking advantage of the probes that the patient has; as well as avoiding infections derived from the use of probes.

DETAILED DESCRIPTION

Figure 1:
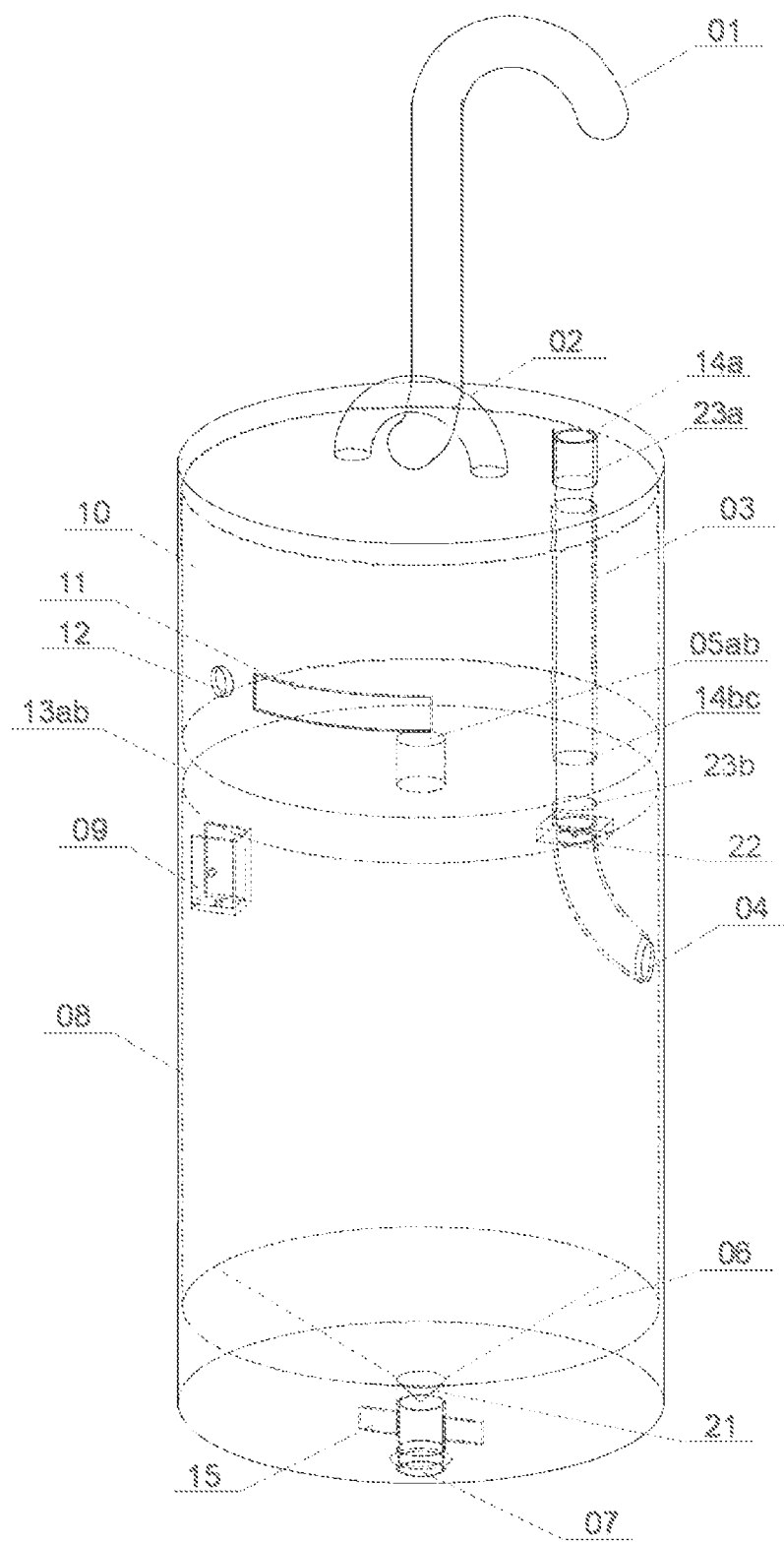
FIG. 1 corresponds to a front view of the body fluid measurement module in which the fastening elements can be seen, that is, a hook (1) and an articulated support (2); the electronic module (10); and the disposable container (8); as well as some of the parts of these components.

The present disclosure relates to a device for the prevention of infections and the measurement of body fluids. This device is made up of at least two modules: a first module corresponding to the body fluid measurement module, and a second module corresponding to the infection prevention module. In some embodiments, the body fluid measurement module comprises an electronic module (10), a disposable container (8), a fluid circulation tube (27) and a disposable container. In some embodiments, the probe infection prevention module comprises a conical shaped sheet with adhesive sections to form the conical structure, to adhere to the probe and to the skin or mucosa of the patient.

In some embodiments, the body fluid measurement module may be fixed to a rigid, fixed, or mobile structure, close to the location of the patient by fastening means. In some embodiments, fastening means comprise hooks (1) and supports (2), where the supports (2) may be articulated, which allows accommodation of the device without affect the comfort or ergonomic position of the patient.

Figure 2:
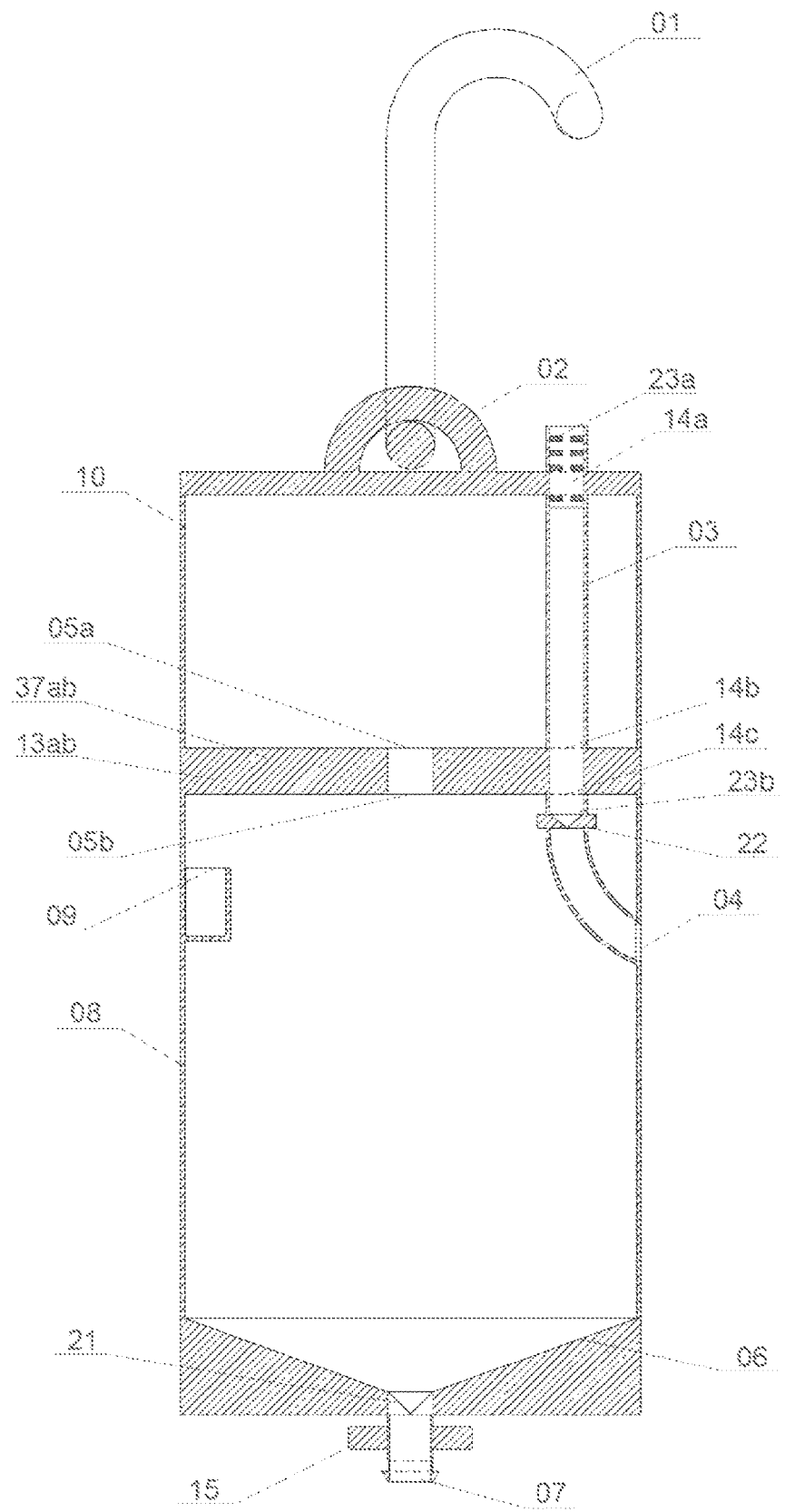
FIG. 2 corresponds to a cross section of the module previously represented in FIG. 1. In this section the arrangement of the upper (5a) and lower (5b) windows, the adjustment of the internal and external threads to form the hermetic closure (13ab) between the electronic module (10) and the disposable container (8), as well as the arrangement of the tunnel (3) that allows the coupling of the fluid circulation tube (27) may be appreciated.
Figure 3:
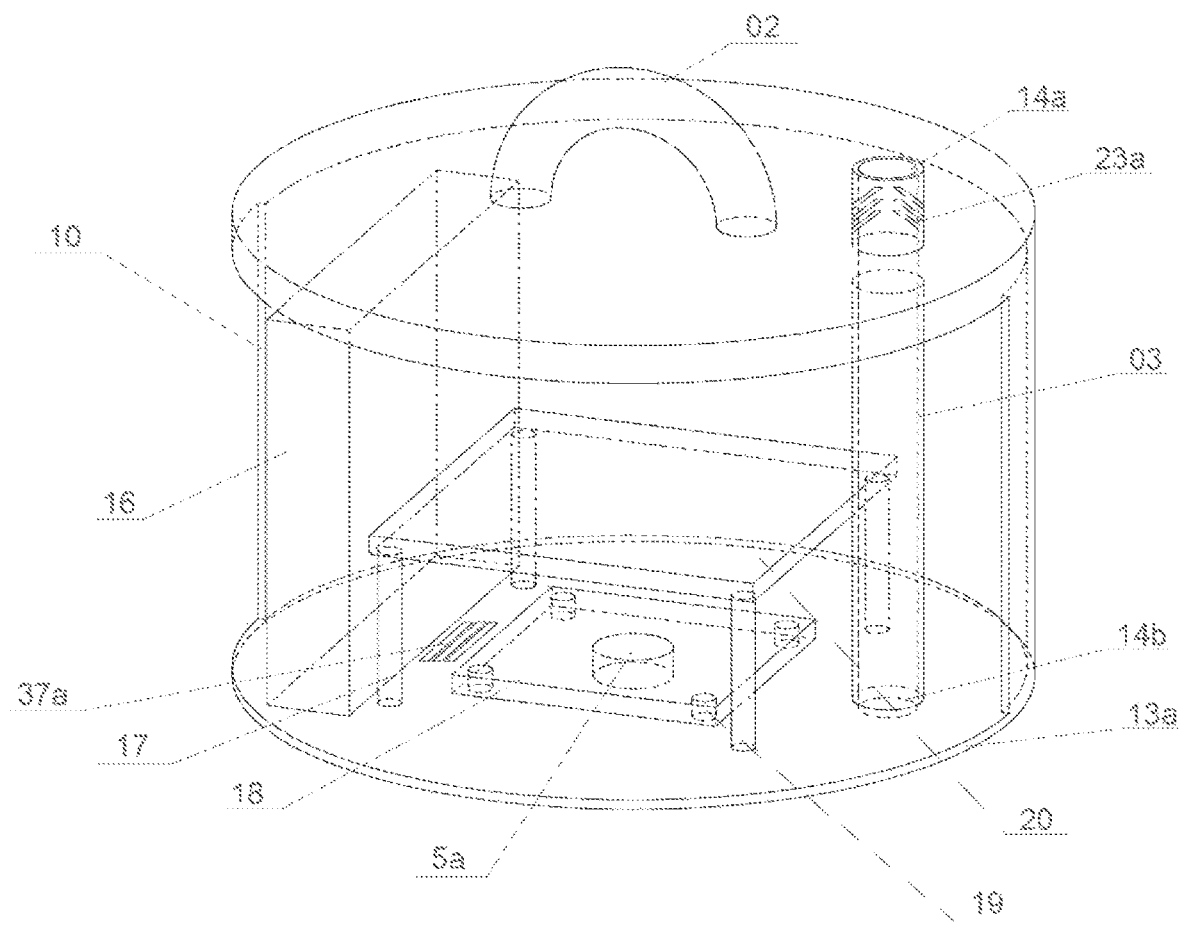
FIG. 3 illustrates the electronic module (10) with all its components. How the tunnel (3) is traversed may be appreciated; and furthermore, a possible spatial distribution of the components of the electronic module (10) is exemplified.

The electronic module (10) can be seen in detail in FIG. 3. Said module (10) may be located in the upper part of the body fluid measurement module, immediately below the assembly made up of the hook (1) and the articulated support (2) illustrated in FIGS. 1 and 2. The electronic module (10) is non-disposable and comprises an upper surface which joins, in the upper part, to the assembly formed by the hook (1) and the articulated support (2), so that by means of these elements the device is supported, for example, from the patient's bed. Furthermore, said electronic module may be made in a cylindrical shape, complementing the possibility of rotation, without discomfort for the patient, provided by the articulated support (2).

In some embodiments, the electronic module (10) is traversed and isolated by a tunnel (3), which allows the introduction of the fluid circulation tube (27); for the purposes of the arrangement of the tunnel (3) that passes through the electronic module (10), the upper and lower surfaces of said electronic module (10) may comprise holes, that is, the upper surface of the electronic module (10) may comprise an upper tunnel hole (14a), while the lower surface of the electronic module (10) may comprise a lower tunnel hole (14b). In some embodiments, upper tunnel hole (14a) may be aligned with the coupling system (locking and unlocking system) (23a) of the fluid circulation tube (27), selected from an incomplete internal thread, which will connect with an incomplete external thread (28c) of the fluid circulation tube (27), as will be explained later.

Likewise, the electronic module (10) may comprise an LCD screen (11) and may further comprise one or more on, off, and command buttons (12). In some embodiments, the screen (11) and the buttons (12) may be located in a part visible to the operator of the device. In some embodiments buttons (12) may be located in the middle area of the external cylindrical surface of the electronic module (10), as illustrated in FIG. 1.

Additionally, the electronic module (10) may comprise a battery (16), which in some embodiments may be rechargeable, which energizes the electronic system (20) for the measurement of fluids; a support (17) that allows the incorporation and adjustment of the electronic system (20); supports (19) for the laser sensor (18); the electronic system (20); the laser sensor (18), which may be aligned with an upper window (5a); an electrical coupling (37a) of the electronic module (10) may be located on the lower wall of the electronic module (10), which can have electrical contact with the electrical coupling (37b) of the disposable container (8), forming the coupling (37ab), which allows the passage of electric current for the activation of the electromechanical valves (21) (22), which will be discussed later; an upper window (5a) for the laser sensor (18), which is located in the central part of the surface or lower wall of the electronic module (10) and allows the visualization of the measurement conditions; and an internal thread (13a) in the edge of the lower wall of the electronic module (10), which allows the hermetic coupling of the electronic module (10) with the disposable container (8).

In some embodiments, sensor (18) is a laser level measurement sensor, and in this sense it transmits an electromagnetic signal for its subsequent reflection in a fluid, so that it is possible to indirectly measure the level of a liquid by measuring a time elapsed between the emission and the detection of an electromagnetic wave of a predetermined wavelength. In some embodiments, collected data may be processed by the electronic system (20), which consists of a set of hardware and software, which, among other functions, may transmit the information to the user through a selected output means such as LCD screen (11), a USB port, or a Wi-Fi wireless system for data transmission to a selected computer device, smart cell phone, or the like. In some embodiments, data transmission uses an encryption protocol where the encryption protocol is selected from TLS, SSL, SSH, among other encryption methods and among other information output means. In some embodiments, electronic system (20) may generate an automatic response in the electromechanical system, that is, in the valves (21) (22), thereby allowing the passage of the fluid, either to allow the entry or exit of the disposable container (8). In some embodiments, electronic system (20) allows the reading and processing of data and comprises electronic and instrumentation elements selected from accelerometers, gyroscopes, sensors, microprocessors, external memories, ports for external memory, switches, among others.

In some embodiments, disposable container (8) may be hermetically coupled with the electronic module (10) by means of an external thread (13b), which may be coupled with the internal thread (13a) located on the lower wall of the electronic module (10), forming a hermetic closure (13ab), as can be seen from what is illustrated in FIG. 2. In some embodiments, disposable container (8) may comprise in its upper wall a lower window (5b) which is aligned with the upper window (5a), as illustrated in FIG. 2; for this purpose, the disposable container (8) may be located centrally on said upper wall. In some embodiments, the aligned arrangement of the upper (5a) and lower (5b) windows allows the flow of electromagnetic waves in both directions.

Figure 4:
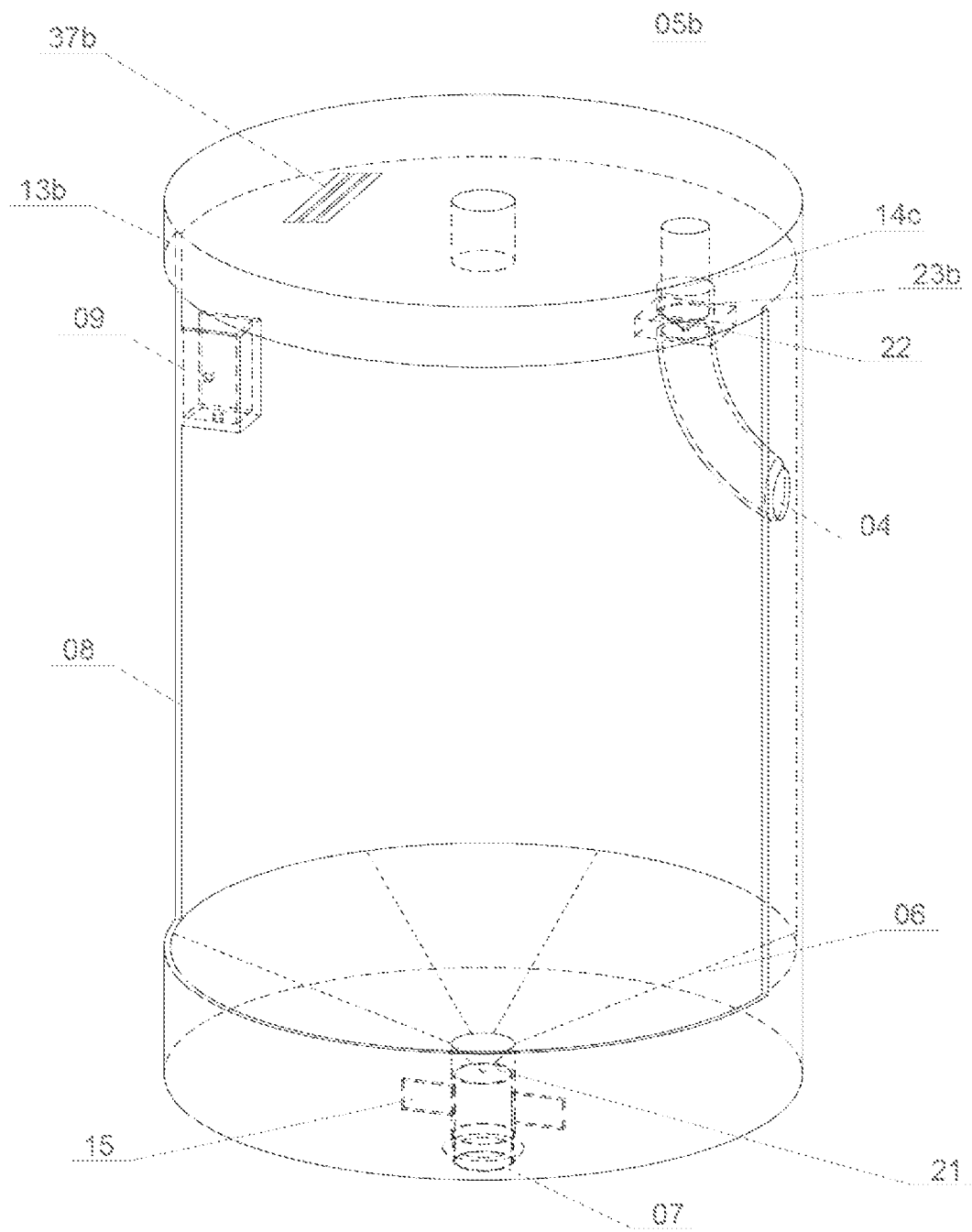
FIG. 4 illustrates the disposable container (8). In this figure it may be seen that the upper wall of the container (8) comprises an electrical coupling (37b) and the lower window (5b) that allows the flow of light from a laser (18). Likewise, the ventilation system (9) is evidenced, on one of the walls of the container (8) equipped with interposed columns that allow directing the fluids. In the upper portion of the container (8) the lower coupling (23b) of fluid circulation tube (27) is also observed, followed by the upper solenoid valve (22) and the channel (4) that directs the fluids towards a wall of the container (8). At the bottom of the container (8) is the funnel (6) that channels the fluids to the lower solenoid valve (21).

In some embodiments, disposable container (8), illustrated in FIG. 4, on its upper face may comprise an inlet hole (14c), which is aligned with the lower hole of the tunnel (14b), as well as with the fixing and hermetic closing system (23b) of the fluid circulation tube (27). This hole allows the fluids to exit towards the final waste disposal container. Likewise, in some embodiments the upper sector of the disposable container (8) comprises holes for ventilation (9), which may be located on the wall opposite the area near the fluid circulating tube (27). In some embodiments, ventilation holes (9) facilitate the circulation of air between the container (8) and the environment in such a way that the production of voids due to the exchange of fluids between components such as the container (8), the fluid circulation tube (27), and the disposable bag is inhibited.

Below the inlet hole (14c) of the disposable container (8) in some embodiments there may be an upper solenoid valve (22), which regulates the flow of fluids from the fluid circulation tube (27). This solenoid valve (22) may be in contact with a channel (4) that conducts the fluid towards the wall of the disposable container (8), said orientation prevents the free fall of the fluid, thus helping to reduce turbulence and possible splashes.

In the lower portion of the disposable container (8) in some embodiments there may be a conical structure (6) that channels the fluid, interacting with a funnel, towards the lower solenoid valve (21), which regulates the outlet of the fluid towards the reservoir bag. In some embodiments, outside the lower wall of the container may be the coupling system (15) for the reservoir bag and the fluid outlet nozzle (7).

Figure 5:
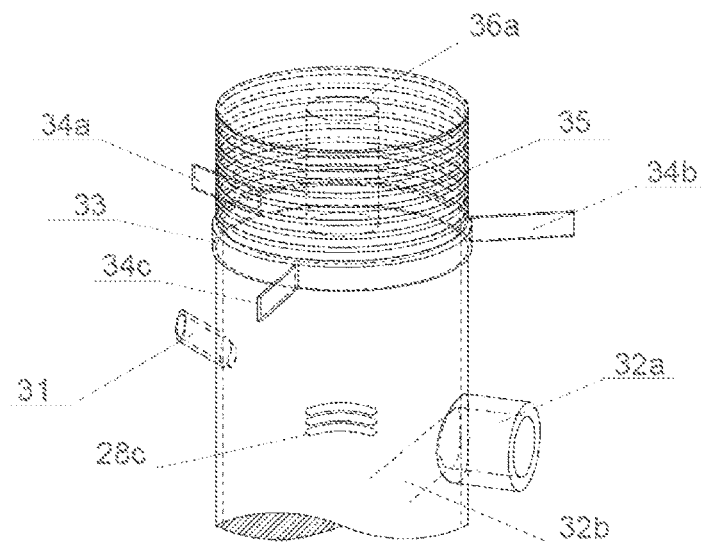
FIG. 5 shows in detail the components of the fluid circulation tube (27). In this embodiment of the system and methods discussed herein, three bars of antimicrobial gel (30a) (30b) (30c) are arranged between the upper (29b) and lower (29a) anti-reflux valves.
Figure 5:
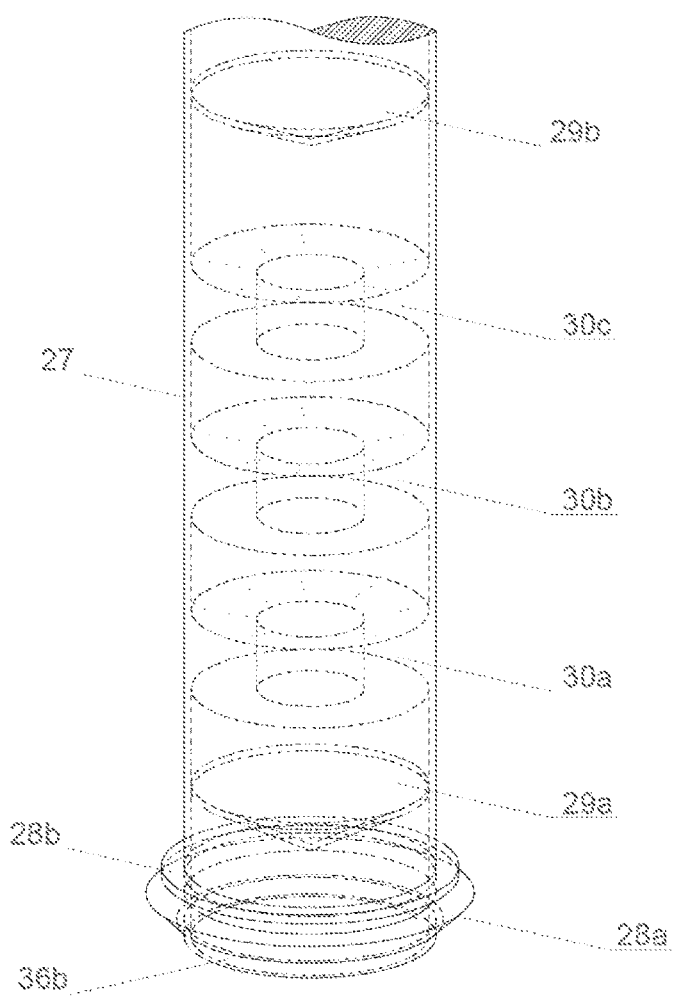

In some embodiments, fluid circulation tube (27), illustrated in FIG. 5, may comprise an upper hole (36) associated with an expandable connector for the probes (35) which opens after applying pressure with the tip of the different probes, after which, may come into direct contact with multiple microfilaments (36), that is, with higher points directed in the same direction as the passage of the probes. Likewise, in some embodiments the fluid circulation tube (27) comprises an expandable cap (33), which in turn comprises adhesive tapes, for example, those identified as (34a) (34b) (34c), incorporated to fix to different probe types. In some embodiments, after fully extending the expandable cap (33), the adhesive tape strips (34a) (34b) (34c) may remain with the adhesion areas exposed.

Optionally, the device according to some embodiments of the system and methods discussed herein may comprise a connector (32a) for the negative pressure system (47), which is selected from a thread that connects to the internal thread of the negative pressure system (47). This connector (32a) may project downwards through a channel (32b), in order to prevent the flow of the different body fluids towards the negative pressure system (47).

Figure 9:
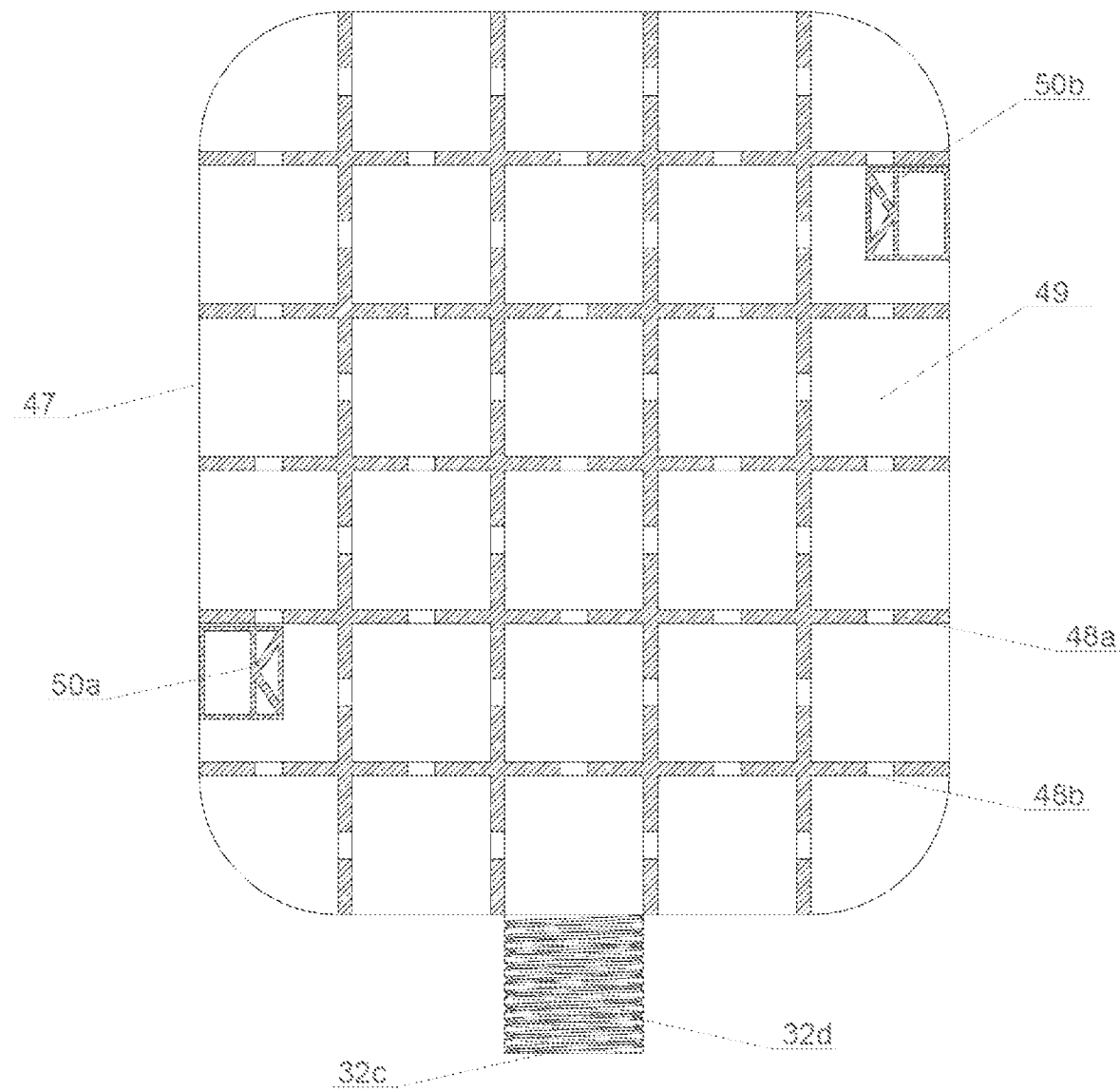
FIG. 9 illustrates the negative pressure system (47) in which the one-way valves (50a) (50b) that allow air to escape can be observed; the cells (49) delimited by the discontinuous walls (48a), as well as the 10 holes (48b).
Figure 10:
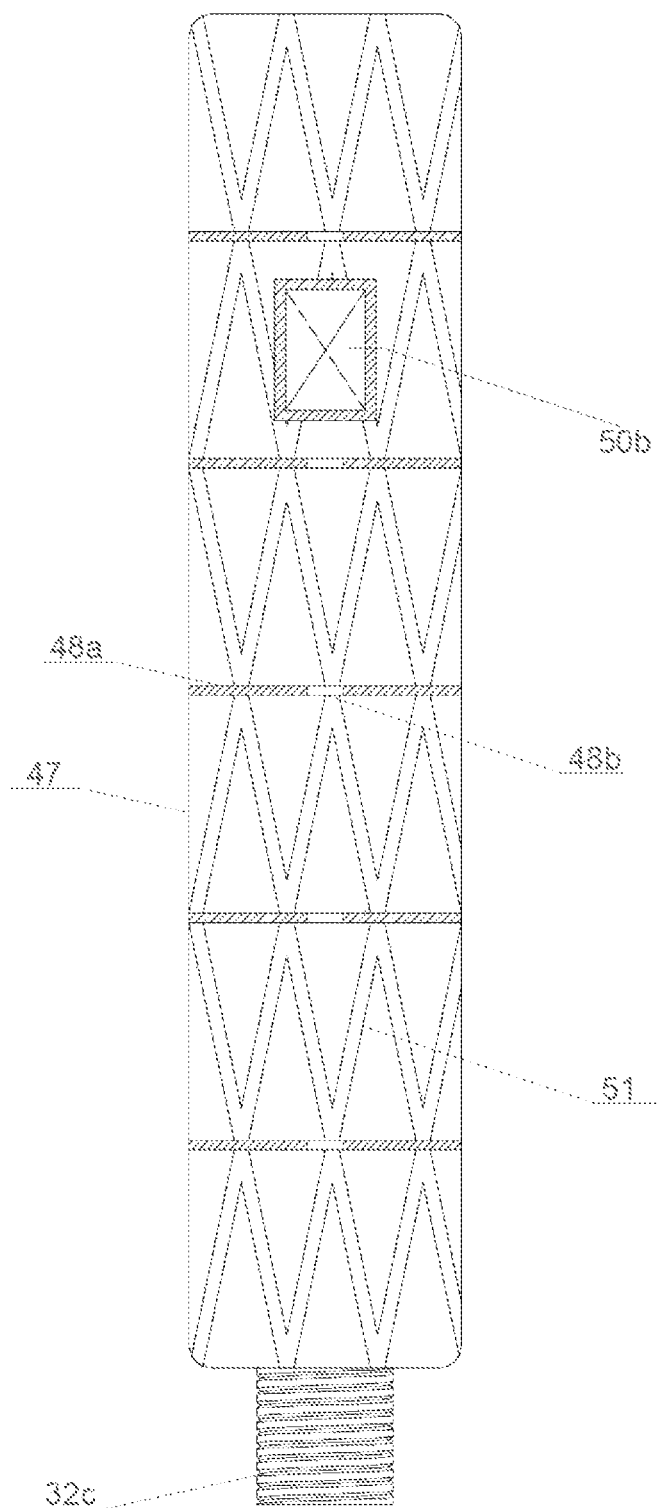
FIG. 10 shows the negative pressure system (47), where each of the cells (49) is equipped with springs (51), which mechanically collapse from the outside, triggering a vacuum and negative pressure system.
Figure 11:
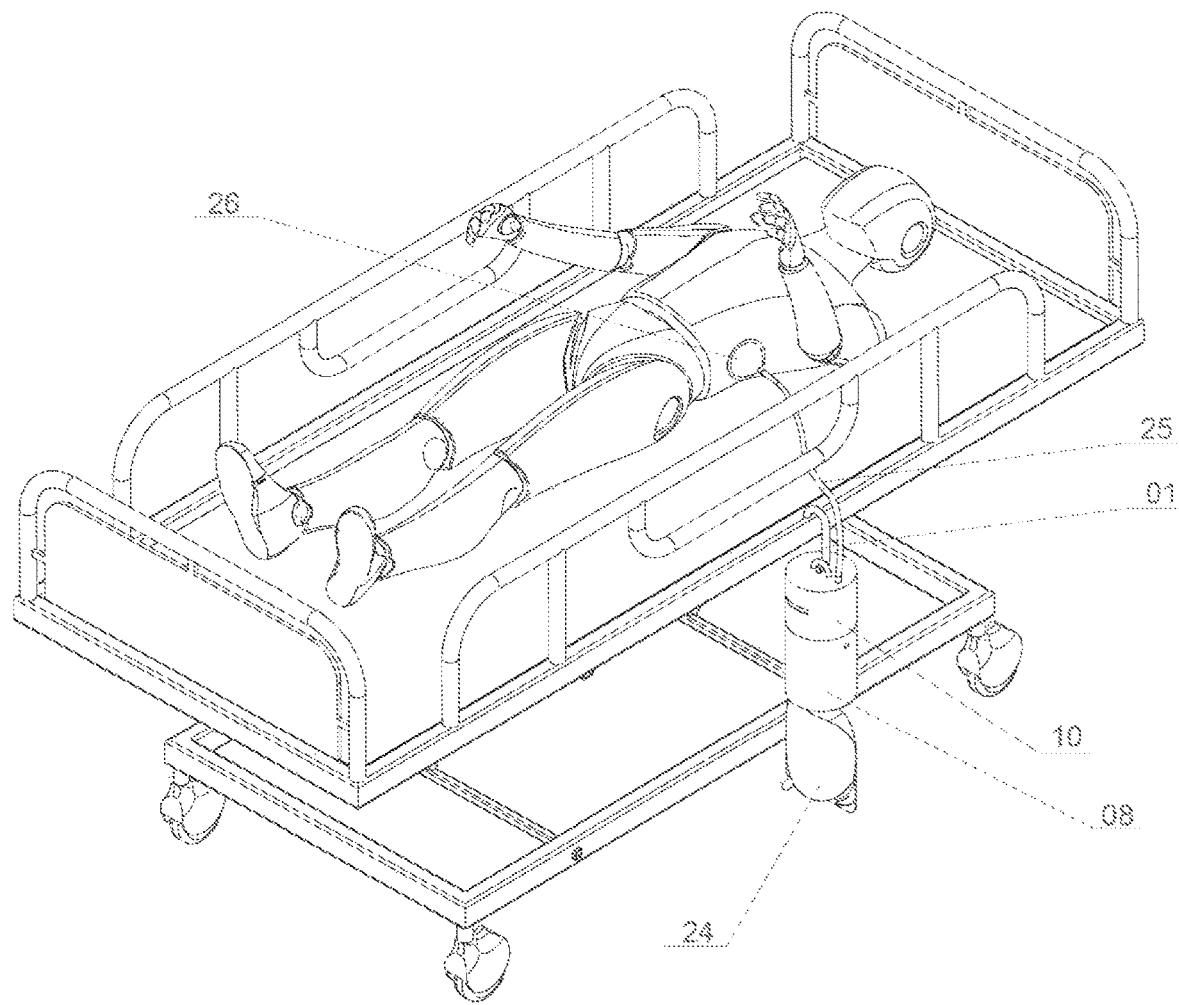
FIG. 11 details the relationship of the patient with the device according to some embodiments of the system and methods discussed herein. Attached to the patient is the probe infection prevention module (26) which also fixes the probe (25) and contains the antimicrobial gel. The fluid measurement module is supported and fixed to the bed through a hook (1) at the base of which there is an articulated support (2) that allows proper alignment of the device. Likewise, the collection bag (24) is observed, a disposable reservoir bag for the temporary storage of body fluids.

In some embodiments, negative pressure system (47), of which two possible modalities are illustrated in FIGS. 9 and 10, comprises an orifice for its interconnection with the fluid circulation tube (27), which continues with an internal thread (32d) that fits hermetically with the external thread or connector (32a) comprised by said fluid circulation tube (27). In addition, in some embodiments the negative pressure system (47) comprises at least one unidirectional valve (50a) (50b), each of which can be located at the bottom and/or top of the negative pressure system (47) and only allows air to exit from the device. In some embodiments negative pressure system (47) is shaped and segmented by means of cells (49), where each cell (49) may be delimited with the others by means of discontinuous walls (48a) by interposed holes (48b) that interconnect them, thus forming a fenestrated interconnection system, or reticular type system, which allows maintaining the stable negative pressure. Likewise, in some embodiments each cell (49) may be equipped with springs (51), which are mechanically collapsed from the outside, triggering a vacuum system and negative pressure that is transmitted to the entire device and to the probes.

In some embodiments, below the expandable cap (33), and the connector (32a) to the negative pressure system (47) when the embodiment comprises it, an incomplete external thread (28c) is located, illustrated in FIG. 5, which is coupled to the coupling system (locking and unlocking system) (23a) of the fluid circulation tube (27), illustrated in FIG. 3. In some embodiments, inside the fluid circulation tube (27) and under the thread (28c), there is a first safety valve (29b) or upper anti-reflux safety valve (29b), where said valve can correspond to a one-way valve. This valve allows the passage of the fluid coming from the probe, but prevents the fluids from backing up towards the probe due to the effect of the fluid pressure. In FIG. 5, between the incomplete external thread (28c) and the upper anti-reflux safety valve (29b) two segmented lines are illustrated, which indicate that the fluid circulation tube (27) can have any length.

In some embodiments, under the anti-reflux safety valve (29b) one or more gel bars (30a) (30b) (30c) may be arranged, arranged one after the other, spaced from each other, where said gel bars (30a) (30b) (30c) can comprise antimicrobial agents, active principles, and excipients, with the function of preventing the rise and colonization of microorganisms that come from the internal part of the system.

Microbial agents correspond to those active principles, or drugs that comprise them, whose function is to prevent colonization and infection by selected microorganisms of, but not limited to, bacteria, fungi, viruses, among others.

In some embodiments, in the lower part of the fluid circulation tube (27), after the section comprising at least one gel bar (30a) (30b) (30c), there may be a lower safety and anti-reflux valve (29a), followed by a security ring (28b), which avoids the loss of relationship at the time of crossing the tunnel, that is, it fixes the catheter at the end of the tube to prevent it from returning and closes it hermetically. Finally, in some embodiments the circulation tube may comprise a lower hole (36b).

Figure 12:
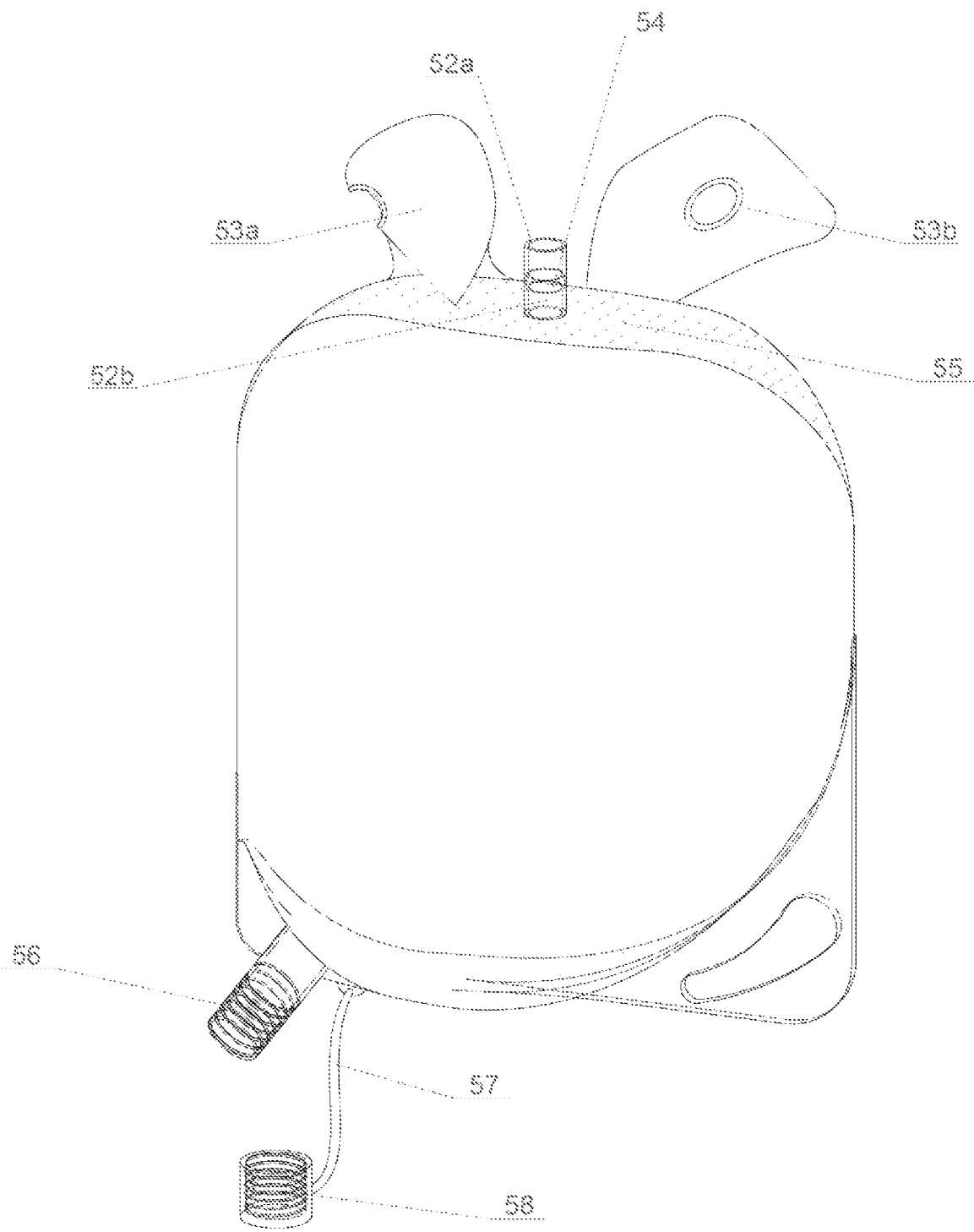
FIG. 12 illustrates the disposable reservoir bag (24) for the temporary storage of body fluids in which some of its components are illustrated such as a tube (56) with external thread, the strap (57) that holds a screw cap internal thread (58) for the hermetic closure of the tube (56) with external thread, the reinforcement material (55) and two hooks, one left (53a) and one 30 right (53b), for the support of said bag (24).
Figure 13:
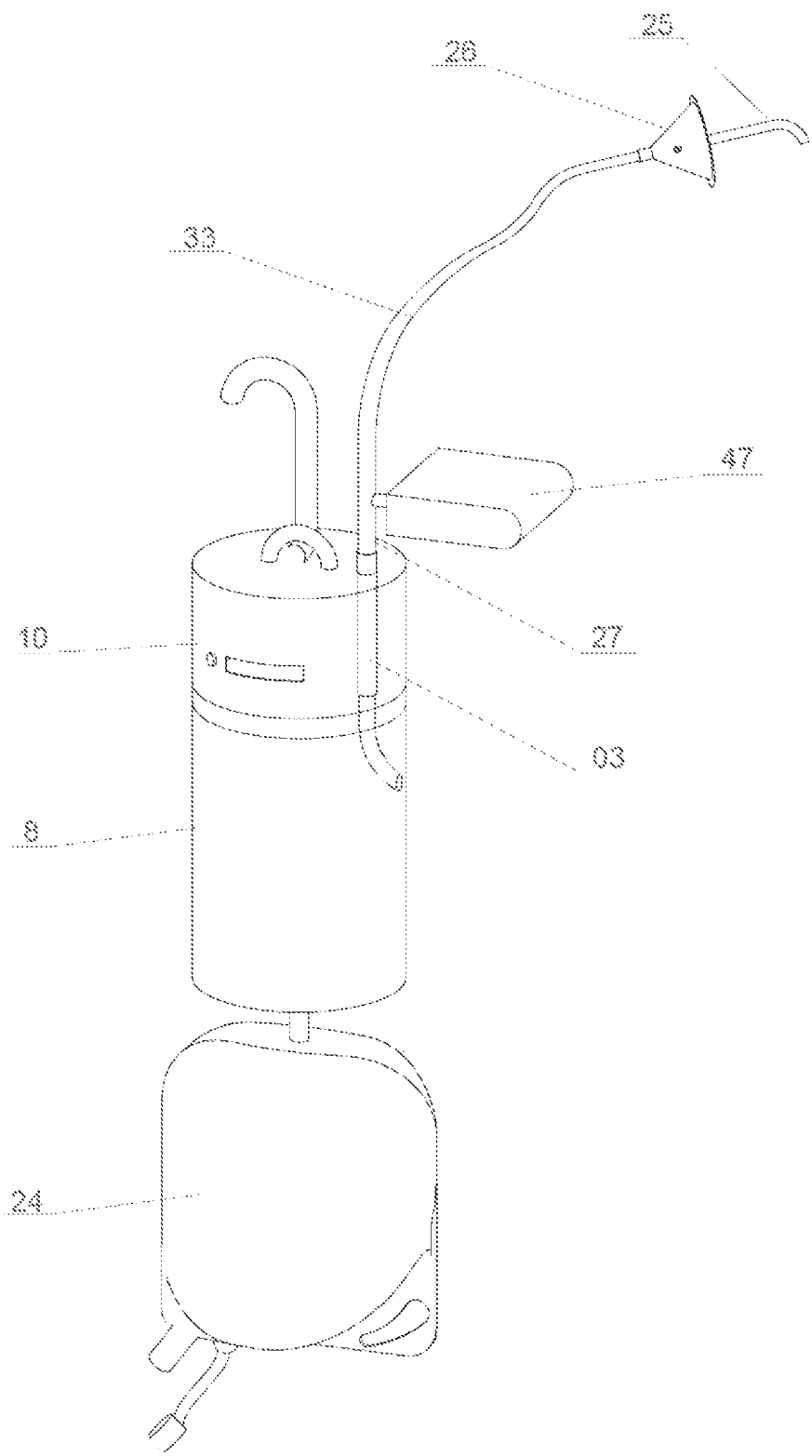
FIG. 13 illustrates a complete view of the device for the prevention of infections and the measurement of body fluids.

In some embodiments the fluid measurement module is complemented with a disposable container for the final disposal of fluids illustrated in FIG. 12. In some embodiments, the disposable container may comprise a disposable reservoir bag (24) for the temporary storage of body fluids, as well as a coupling system and a drainage system for stored fluids.

In some embodiments the coupling system of the disposable container may include an upper hole (52a); a coupling, fixing and hermetic closure system (54), which follows the upper hole (52a) and may be coupled both to the outlet nozzle (7) of the disposable container, and to the gasket (28a) of the fluid circulation tube (27); and, a lower hole (52b) that allows the flow of the biological waste.

In some embodiments, the drainage system of the disposable reservoir bag (24) may be located in the lower part thereof and comprises a tube (56) and may comprise an external thread that allows the fluid contained in the bag (24) to pass, for example, to another container. Likewise, it may comprise a strip (57), located next to the tube with external thread (56), which may hold a cap with internal thread (58) for the hermetic closure of the tube (56) with external thread.

In one embodiment, the upper part of the reservoir bag (24) comprises a reinforcement (55) of the material, to which two hooks are attached, one left (53a) and one right (53b), for the support of said bag (24), where the hooks (53a) (53b) are fixed to the coupling system (15) of the disposable container, or to a disposable hook to be able to be fixed to the bed or other structure.

As can be seen, in some embodiments the coupling, fixing and sealing system (54) can be coupled both to the outlet nozzle (7) of the disposable container, and to the gasket (28a) of the fluid circulation tube (27); so that the disposable reservoir bag (24) can be connected to the disposable container (8) or to the fluid circulation tube (27).

In an embodiment, the reservoir bag (24) in the lower part comprises a drain cock to evacuate the stored fluids.

The device may comprise a module to prevent infections for probes. In some embodiments in the fluid flow measurement module there may be a section that minimizes the colonization of microorganisms during the procedure in which the fluids to be measured are being generated, which may be included in the fluid circulation tube (27) and corresponds to the provision of anti-reflux safety valves (29a) (29b) and one or more antimicrobial gels (30a) (30b) (30c).

Figure 6:
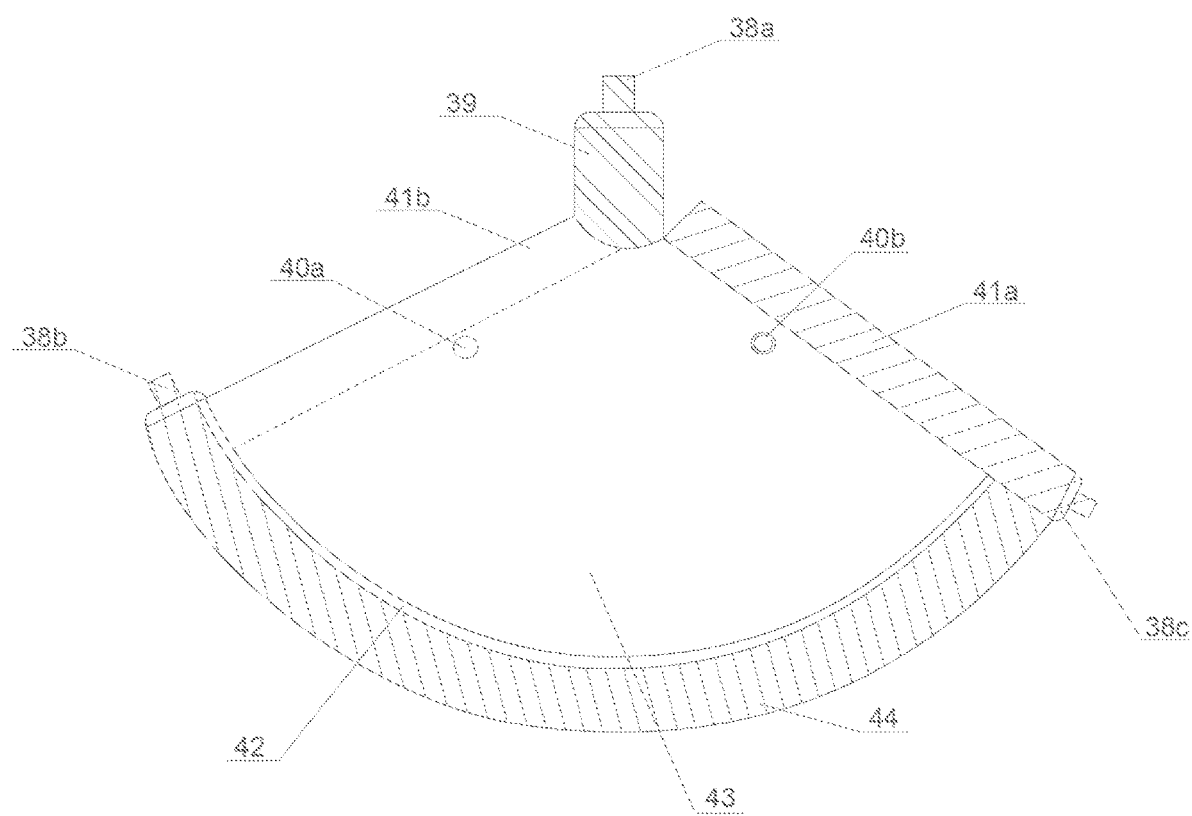
FIG. 6 shows the shape of the sheet, as well as the adhesive areas (39) (41) (44), which allow the formation of the conical structure (41), adhesion to the skin and/or mucosa of a patient (44), as well as the binding to the probe (25). Similarly, the expandable connector (40b) and its insertion site (40a) of the connector through which the syringe (46) passes are shown.
Figure 7:
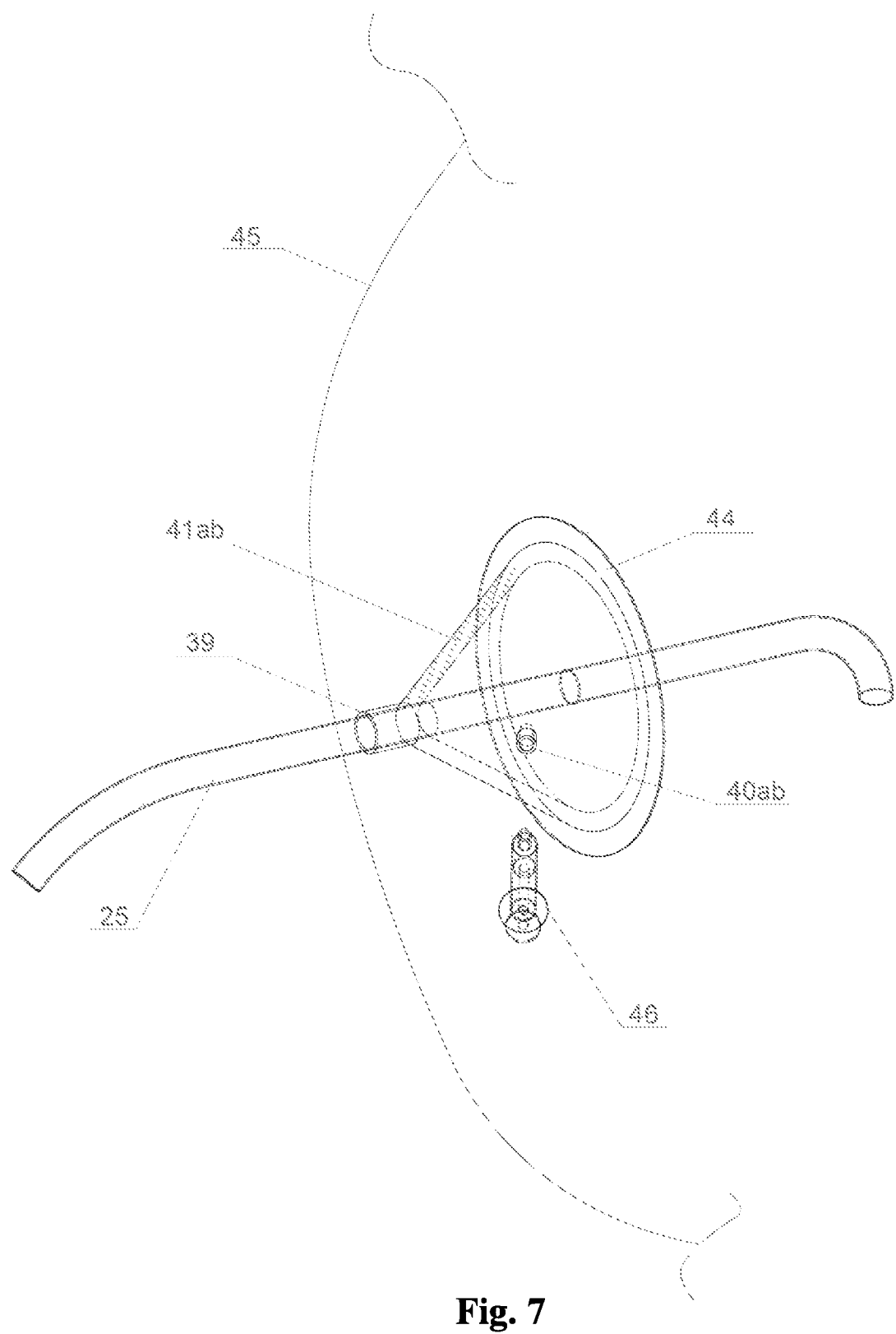
FIG. 7 illustrates the fully formed probe infection prevention module adhered to the skin or mucosa of the patient. This view shows the volumetric relationship between the surface of the skin and/or mucosa (45) with the probe (25). The internal portion of the probe (25) can also be seen in a discontinuous line, which is found within some human tissue and the relationship of the aligned expandable connector (40ab) with the syringe (46).
Figure 8:
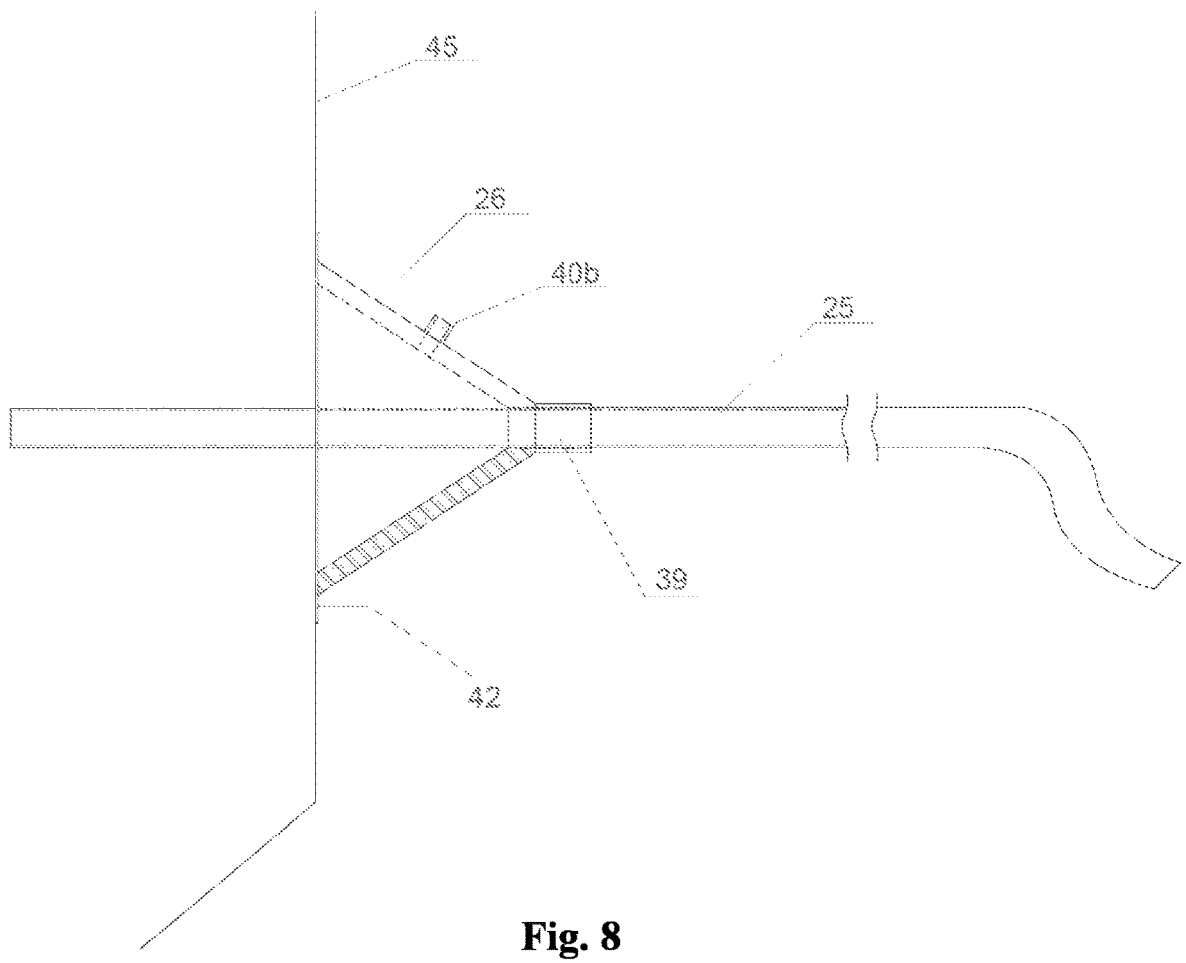
FIG. 8 shows the fully formed probe infection prevention module adhered to the skin or mucosa of the patient. This schematic side section also shows the relationship of the different parts of the probe infection prevention module (26) with the surface of the skin and/or mucosa (45) and the probe (25). The band (42) that delimits and reinforces the upper end of the base (44) may be appreciated.

In some embodiments, the module to prevent probe infections, illustrated in FIGS. 6 to 8, corresponds to an elastic material pre-cut so as to allow the formation of a structure with a conical shape, which adheres to the probe and to the skin or mucosa. In some embodiments, the pre-cut elastic material may have a triangular shape where one of its sides is convexly curved and the vertex opposite the convex side is curved with a concave termination. In some embodiments, the module to prevent infection by probes comprises at least three adhesive tapes (39) (41) (44) and strips (38a) (38b) (38c) that protect the corresponding adhesive section. In some embodiments, the elastic material cut to form a conical structure is arranged over the probe inserted into the patient forming a cone.

In some embodiments, the arrangement of the adhesive tapes allows the formation of the conical structure. In such embodiments, an adhesive tape is arranged on a straight side of the elastic material (44) and allows the formation of a conical shaped structure; an adhesive tape is arranged on the vertex opposite the curved side of the elastic material (39) and allows adhesion to the probe (25); while an adhesive tape allows it to be attached to the skin or mucosa of the patient (41) and is arranged on the curved side of the elastic material.

In certain embodiments, the module to avoid infection comprises the sections marked in FIG. 6. First, the strip of the cone (38c), uncovering the adhesive portion (41a) of the tape (41) of the cone; this exposed adhesive zone is located on the contralateral side, in the adhesion zone (41b), which is demarcated with a broken line. Adjacent to the adhesive tape of the cone is the expandable connector (40b) for the syringe (46), which allows the injection of a gel (43) into the container; on the contralateral side, properly aligned and adjacent to the adhesion zone, is the hole for this connector (40a). In some embodiments, connector (40a) and its insertion site (40b) provide an accurate guide for the formation of the cone. Subsequently, the base of the module may be formed: after pulling the base strip (38b), the adhesive tape is removed from the base (44), which is delimited and reinforced at its upper end by a band (42) that, additionally, facilitates the conical formation. This exposed area adheres to the skin and/or mucosa. Finally, the tip of the module may be formed to prevent infection; after pulling the tip strip (38a) the adhesive tape is removed from the tip (39) and proceed to adhere and fix the tip to the patient probe.

In some embodiments, probe infection prevention module comprises an expandable connector (40b) and an insertion site (40a) of the expandable connector (40b), which once assembled allow the entry of the tip of a syringe (46) containing antimicrobial gel (43).

In one embodiment, the probe infection prevention module allows coupling an iterative fractal system of variable electromagnetic fields (IFSVEF) which could contribute to a better gel activity due to the interaction with the electric current. The energy for the IFSVEF comes from the electronic module (10) of the body fluid measurement module.

The figures presented in this description correspond to merely illustrative purposes of some embodiments of the system and methods discussed herein. It is understood that the described figures do not limit the scope of the disclosed invention. A person skilled in the art is capable of conceiving subsequent modifications to the embodiments disclosed in this document.

Although some embodiments of the invention are described in the present description, it will be appreciated that numerous modifications and other embodiments may be devised by those skilled in the art subsequent to the disclosure of the present invention. For example, the features described herein can be applied in other embodiments. Therefore, it will be understood that the claims are intended to cover all modifications and embodiments that are within the spirit and scope of the present disclosure.

What is claimed:

1. A device for prevention of infections and measurement of body fluids comprising a module for non-invasive measurement of fluids leaving the human body and a module for prevention of infections caused by probes, wherein the modules are interdependent and complementary; and the module for non-invasive measurement of fluids comprises:
   fastening elements selected from a hook and articulated supports that allow adequate alignment, support and accommodation of the device,
   a non-disposable electronic module for continuous measurement of generated body fluids, the electronic module being traversed and isolated from the fluids by a tunnel that allows introduction of a fluid circulation tube, and comprises an upper window, a rechargeable battery that generates electric current, a hermetic coupling, an electrical coupling for coupling with a disposable container, a locking and unlocking coupling with the fluid circulation tube, a level measurement laser sensor aligned with the upper window and the disposable container that allows indirect measurement of a level of a liquid by measuring a time elapsed between emission and detection of an electromagnetic wave of a predetermined wavelength, and a digital electronic system with instrumentation and control elements, performing data storage, processing and transmission,
   a disposable container for temporary retention of fluid during the measurement, said disposable container being alignable with the laser sensor, the disposable container comprising a lower window, with hermetic and electrical coupling with the electronic module and comprises a channel, a funnel, ventilation holes, and solenoid valves that guarantee adequate flow that can be measured and mechanically prevent microorganisms from rising from the disposable container and rise of contaminated fluids,
   a fluid circulation tube arranged between a patient probe and the disposable container communicating the fluid between said probe and said container, the fluid circulation tube comprising an expandable cap that avoids direct contact of external environment with the probes, an expandable connector for anti-reflux probes that limits rise of microorganisms, lower and upper anti-reflux safety valves that limit rise of contaminated fluids and microorganisms, one or more bars of antimicrobial gel that prevents generation of infections inside the device and an incomplete external thread which is coupled to a coupling system, and
   a disposable collector for final disposal of biological waste, the collector comprising a coupling, fixing and hermetic closure system coupled to an outlet nozzle of the disposable container and packaging of the fluid circulation tube, and
wherein the module for prevention of infections caused by probes comprises:
   a cone, which adheres to a probe, skin or mucosa and prevents passage of microorganisms,
   an expandable connector for entry of a tip of a syringe containing an antimicrobial gel, and
   an antimicrobial gel located in the cone, wherein said gel prevents generation of infections at a point of entry of the probe to a patient.

2. The device for preventing infections and measuring body fluids of claim 1, wherein the electronic module comprises an LCD (Liquid Crystal Display) screen and one or more on/off and command buttons.

3. The device for preventing infections and measuring body fluids of claim 1, wherein the electronic module comprises a support of the electronic system, supports for the laser sensor and the upper window is located on a lower wall of the electronic module.

4. The device for preventing infections and measuring body fluids of claim 1, wherein the electronic system allows reading and processing of data, level measurement, volume calculation, determination of the position of the device, control of electromechanical valves, real time measurement, storage and transmission of processed information to an electronic device and includes electronic and instrumentation elements selected from accelerometers, gyroscopes, sensors, microprocessors, external memories, ports for external memory, switches, among others.

5. The device for preventing infections and measuring body fluids of claim 1, wherein the electronic module is hermetically coupled with the disposable container by an internal thread on an edge of a lower wall of the electronic module and an external thread on an edge of an upper wall of the disposable container, wherein the internal thread and the external thread form a hermetic seal.

6. The device for preventing infections and measuring body fluids of claim 1, wherein the disposable container comprises ventilation holes, which facilitate circulation of air between the container and the environment and avoids production of voids due to an exchange of fluids between components such as the container, the fluid circulation tube, and the disposable bag; a fluid inlet hole; an upper solenoid valve that regulates flow of fluids coming from the fluid circulation tube; a funnel that directs fluids towards a lower solenoid valve; and the lower solenoid valve that regulates outlet of fluid towards a reservoir bag.

7. The device for preventing infections and measuring body fluids of claim 6, wherein the disposable container comprises in its upper wall a lower window which is aligned with the upper window, allowing flow of laser light waves in both directions.

8. The device for preventing infections and measuring body fluids of claim 6, wherein the disposable container comprises a channel that directs fluids towards a wall of the container, reducing turbulence and possible splashing as well as level measurement errors.

9. The device for preventing infections and measuring body fluids of claim 1, wherein the fluid circulation tube comprises an upper hole associated with an expandable connector for probes and adhesive tapes to fix different types of probes.

10. The device for preventing infections and measuring body fluids of claim 1, wherein the disposable container for final disposal of fluids comprises a disposable reservoir bag, a fluid circulation tube coupling system and a drainage system for stored fluids, wherein the disposable reservoir bag comprises an upper hole and a lower hole that allows flow of biological waste.

11. The device for preventing infections and measuring body fluids of claim 10, wherein the drainage system of the disposable reservoir bag is located in a lower part thereof and comprises an externally threaded tube with external thread, a strip located next to the externally threaded tube and an internally threaded cap, wherein the strip supports the internally threaded cap and the externally threaded tube forms a tight seal with the internally threaded cap.

12. The device for preventing infections and measuring body fluids of claim 10, wherein the reservoir bag comprises two hooks, to support said bag.

13. The device for preventing infections and measuring body fluids of claim 1, wherein the module for non-invasive measurement of fluids comprises a negative pressure system arranged in connection with the fluid circulation tube and a connector that connects with the negative pressure system and projects down through a channel, preventing flow of different body fluids towards the negative pressure system.

14. The device for preventing infections and measuring body fluids of claim 13, wherein the negative pressure system comprises one-way valves that only allow exit of air from the device; and, being segmented into cells, where each cell is delimited by discontinuous walls having interposed holes that interconnect them.

15. The device for preventing infections and measuring body fluids of claim 14, wherein each cell comprises springs, which mechanically collapse from outside, triggering a vacuum and negative pressure system that is transmitted to the device and to the probes, preventing rise of fluids through the probe.

16. The device for preventing infections and measuring body fluids of claim 1, wherein the module for prevention of infections caused by probes comprises in the cone an elastic material with a triangular shape with one side being curved, adhesive tapes selected from masking tape arranged on a straight side of the material to an elastic that allows formation of a conical-shaped structure, adhesive tape arranged at a vertex opposite a curved side of an elastic material that allows adhesion to a probe and adhesive tape for attachment to skin or patient's mucosa arranged on the curved side of the elastic material.

17. The device for preventing infections and measuring body fluids of claim 1, wherein the module for prevention of infections caused by probes comprises an iterative fractal system of variable electromagnetic fields (IFSVEF), which allows a better activity of gel by interaction with electric current supplied by the electronic module.

* * * * *